United States Patent [19]

Smith et al.

[11] Patent Number: 4,598,709

[45] Date of Patent: Jul. 8, 1986

[54] ELECTROLYSIS MACHINE

[75] Inventors: Margaret M. Smith, Sylmar; David C. Smith, Van Nuys, both of Calif.

[73] Assignee: Clare, Inc., Sylmar, Calif.

[21] Appl. No.: 516,988

[22] Filed: Jul. 25, 1983

[51] Int. Cl.⁴ ............................................. A61B 17/41
[52] U.S. Cl. ................................. 128/303.18; 128/908
[58] Field of Search ................. 128/303.13, 303.14, 128/303.17, 303.18, 908, 419 R, 421, 422

[56] References Cited

U.S. PATENT DOCUMENTS

| 2,444,173 | 6/1948 | St. Pierre | 128/303.18 |
|---|---|---|---|
| 3,989,051 | 11/1976 | Nozhnikov et al. | 128/908 |
| 4,102,347 | 7/1978 | Yuki | 128/421 |
| 4,224,944 | 9/1980 | Roberts | 128/303.18 |
| 4,231,372 | 11/1980 | Newton | 128/303.14 |
| 4,321,926 | 3/1982 | Roge | 128/303.18 |
| 4,372,319 | 2/1983 | Ichinomiya et al. | 128/421 |

FOREIGN PATENT DOCUMENTS 243478 7/1946 Switzerland .................. 128/303.18

OTHER PUBLICATIONS

*Micromatic Solid State Epilator*, R. A. Fischer & Co.
*Electro Blend*, Arthur R. Hinkel.

Primary Examiner—Lee S. Cohen
Attorney, Agent, or Firm—Jack C. Munro

[57] ABSTRACT

An electrolysis machine which utilizes an electrically conductive probe to be physically inserted below the surface of the skin to be located next to a hair shaft within the hair follicle. The electrolysis machine includes two completely separate circuits. One circuit uses a direct current, while the other circuit emits a radio frequency. The amperage of the direct current is controlled to not exceed a certain pre-established value. Upon initial establishment of the circuit with the patient, or re-establishing of the circuit with the patient, surges in electrical current are prevented through the use of a circuit which slows the rise of current to the patient.

2 Claims, 5 Drawing Figures

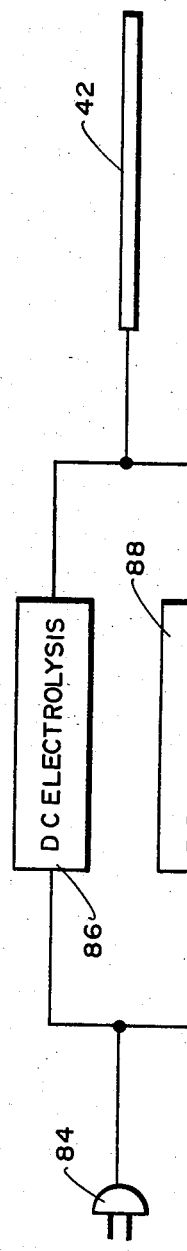
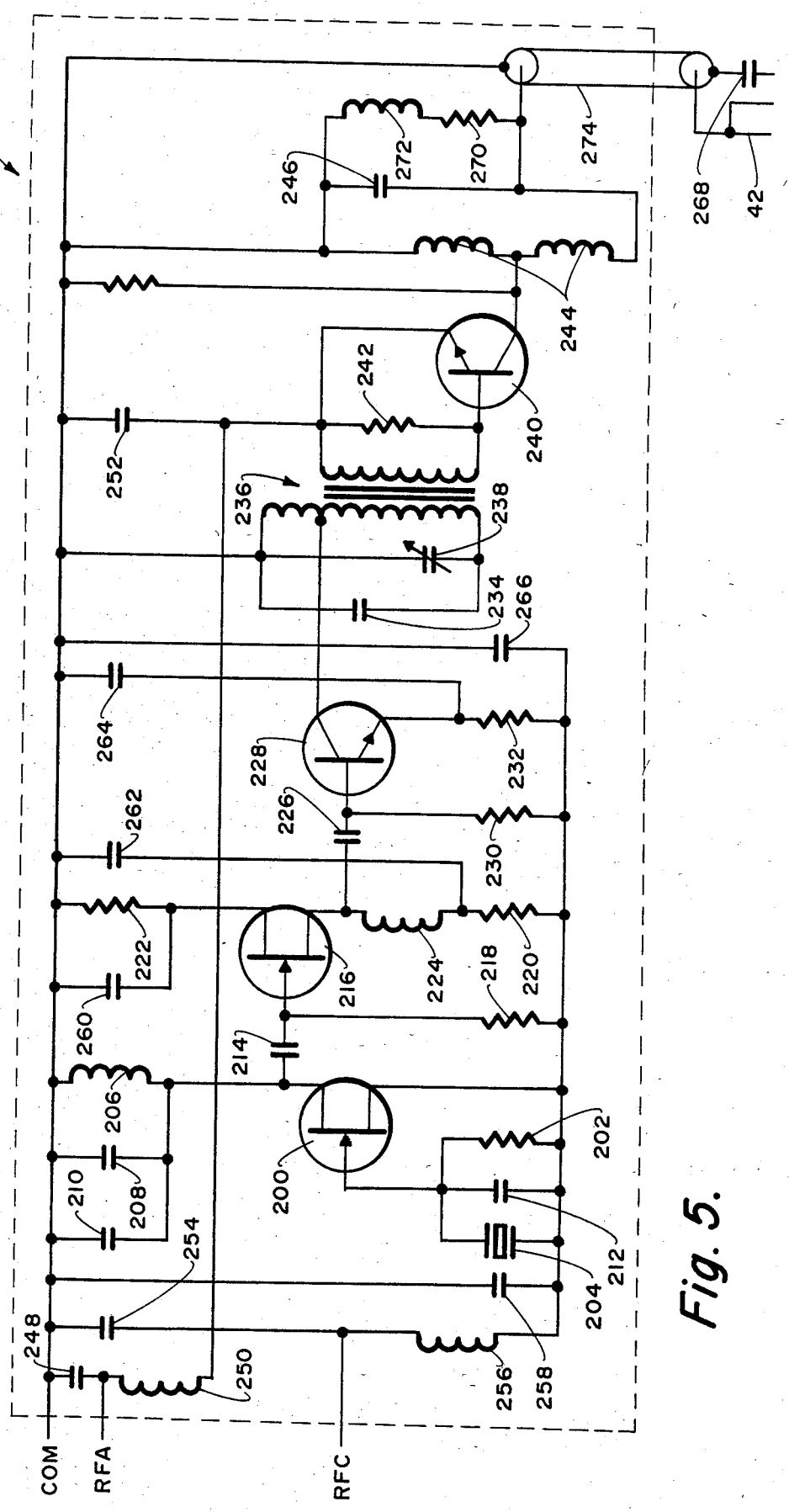
Fig. 3.
Fig. 5.

ELECTROLYSIS MACHINE

BACKGROUND OF THE INVENTION

The field of this invention relates to electrology, and more particularly to an electrolysis machine which is to be usable for permanent removal of undesirable hair on human beings.

Removal of unwanted hair on human beings has long been known. Primarily, hair removal is utilized in conjunction with women. The prime objective of electrolysis is to permanetly remove the hair after a single application. This is normally accomplished by destroying the hair follicle from which the hair grows. This destruction of the hair follicle is to be accomplished with a minimum amount of tissue destruction and also with a minimum amount of pain during application of the technique.

In order to effect permanent removal of a hair, it has been found that the hair must be destroyed from the papilla all the way to the surface of the skin. The destruction has to be performed carefully or tissue scaring will occur causing hard lumps on the surface of the skin, which are unsightly and totally unacceptable.

For a great many years, electrolysis used only a direct current. The direct current tends to flow more quickly to areas where it is more moist, namely the lower portion of the hair follicle. This results in the producing of a chemical reaction, the main product of which is sodium hydroxide, or lye. This sodium hydroxide is caustic and literally eats away at the hair.

Direct current electrolysis causes a low rate of regrowth, which is quite advantageous. However, it has certain disadvantages, in that it takes a substantial period of time (one to three minutes) for each hair follicle. Therefore, considering the wages of an electrologist, direct current electrolysis becomes quite expensive. Also, direct current electrolysis is somewhat painful to the patient.

In recent years, a new electrolysis technique, called "thermolysis" became prevalent. Thermololysis used a probe in the same manner as direct current electrolysis uses a probe. However, with thermolysis, instead of direct current, a high frequency sinusoidal voltage is injected into the follicle. The radio frequency tends to physically cook the follicle thereby dessicating such.

Thermolysis has a primary advantage in that it is exceedingly fast and can be even faster than a tenth of a second for high intensity bursts of radio frequency energy. Thermolysis also has the advantage that it is simple to train an operator to learn this technique. Most often, thermolysis takes three to five seconds, which is an incredible increase over one to three minutes, which is necessary with direct current electrolysis.

Thermolysis also has the additional advantage in that the heating pattern begins at the tip of the probe and spreads with time. This is called the "point effect" and causes the follicle destruction to begin at the very bottom, which is the desirable pattern to follicle destruction.

The disadvantages of thermolysis is that the heating pattern is narrow. It has been generally found that thermolysis has a low reliability factor when used on heavy or curly hair. This is due to the fact that heavy hair follicles are too wide for the heating pattern. In relation to curly hair the follicle itself will curl away from the probe and thereby leave hair follicle areas which have not been destroyed. Any portion of the hair follicle that has not been destroyed will be capable of regrowing.

Most recently, a new technique came to pass which frequently called the "blend" technique. This blend technique combines the direct current technique with the radio frequency technique. The radio frequency technique causes heat in the follicle which increases the rate of chemical action for the direct current. The heat also tends to open the tissue allowing the lye to penetrate the tissue much more quickly. The result is all the reliability and low regrowth rates of the direct current technique has been obtained within a substantially shorter period of time.

Normal treatment time for the blend technique is about twenty to thirty seconds. This is considerably longer than the thermolysis technique by itself, but also substantially shorter than the direct current electrolysis by itself. Also, using the blend technique, uniform reliability throughout all different hair types is obtained.

It is to be kept in mind the time variation in any technique has to do with the pain threshold of a particular patient. If the patient can undergo a higher level of pain, he can then have the hair removed more quickly than another patient that is more sensitive to pain.

SUMMARY OF THE INVENTION

The primary objective of this invention is to construct an electrolysis machine which significantly improves blend electrolysis techniques.

As previously mentioned, one of the main problems in dealing with electrolysis is the pain threshold of the patient. Prior to the establishing of a circuit with a patient, the electrolysis machine "builds up" an initial charge. Upon completing the circuit to the patient, this "build up" of charge is discharged through the patient, shocking the patient and creating a painful sensation. This same surge of electrical energy will occur if the patient becomes detached from the electrical ground and then re-establishes contact with that electrical ground. The electrolysis machine of the present invention has been designed to overcome the initial establishment of the circuit with the patient and also the re-establishment of the circuit with the patient by eliminating any surge of electrical energy in these situations.

Also, in previous electrolysis equipment, the electrical current very quickly grows to its desired level. This quick rise would also shock the patient producing pain. The electrolysis machine of the present invention includes circuitry to provide for a slow rise in the current (one half second to one second) as opposed to a millisecond rise in the current of the prior art electrolysis machines.

BRIEF DESCRIPTION OF THE DRAWINGS

FIG. 3 is a basic block diagram of the electrical circuitry utilized in conjunction with the electrolysis machine of this invention;

FIG. 5 is the electrical circuit diagram for the radio frequency electrical circuit of the electrolysis machine of this invention.

DETAILED DESCRIPTION OF THE SHOWN EMBODIMENT

Figure 1:
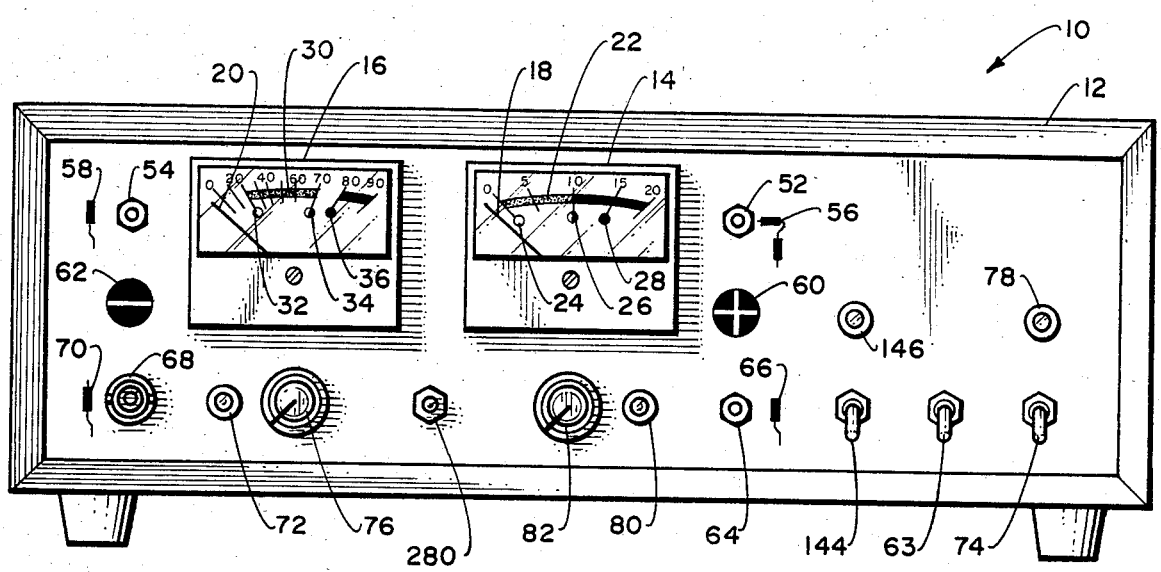
FIG. 1 is a front, elevational view of the electrolysis machine housing of the present invention.
Figure 2:
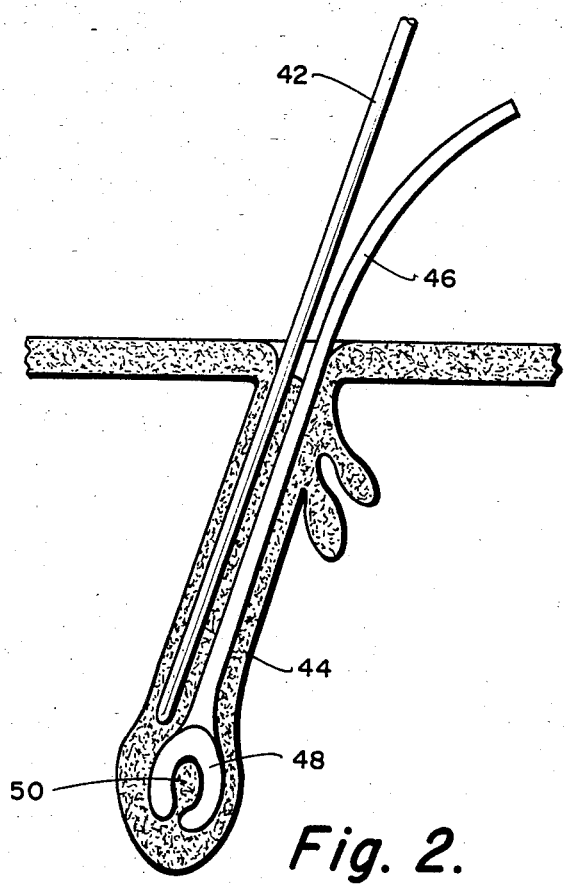
FIG. 2 is a diagrammatical view through a hair follicle showing a probe which is to be electrically connected to the electrolysis machine of FIG. 1 being inserted within the hair follicle.

Referring particularly to FIG. 1 of the drawings, there is shown the electrolysis machine 10 of this invention which is mounted within the housing 12. The front face of the housing 12 has a pair of meter faces 14 and 16 mounted thereon. Meter face 14 has a movable pointer 18, while meter face 16 has a movable pointer 20. The meter face 14 includes indicia in the form of an elongated path 22. Adjacent the path 22 are a series of numerals, such as 0, 5, 10, 15 and 20. Also, the path 22 is divided into individual areas of the same size totaling in number twenty. The meter face 14 is designed to represent milliamperes, which is the current being produced by a direct current circuit located within the housing 12.

Path 22 at the 0 point includes a symbol 24 which is to have a specific meaning, that being to indicate the beginning of the face technic range. A similar symbol 26, which is half colored, is located at the numerical value 10 position on the path 22. To the electrologist, this is the entire face technic range and the pointer 20 is to always remain in this range when working on a patient's face. Between the symbols 24 and 26, the path is colored a specific color, such as orange. This portion of the path, 22 represents between 0 and 10 milliamperes. The face is a sensitive area and therefore requires a lower current that what would be normally used on other portions of the body.

The symbol 28 indicates the most common setting for the body technic range which is located at the numerical position 15. The path between 15 and 20 is color coded a different color, such as green. When the electrologist is removing hair from the body of a human being (other than from the face), normally the pointer 18 will be located between the numerical positions 15 and 20 on the path 22 since the body is not as sensitive as the face.

The meter face 16 includes an elongated path or scale 30 which has a series of numerals, 0, 20, 40, 60, 70, 80 and 90 listed thereby. The meter face 16 is to represent the frequency being utilized within the radio frequency circuit located within the housing 12. On the path 30, at the numerical value 20, there is a symbol 32. A half colored symbol 34 is located on the path at the numerical value of 70. A completely colored symbol 36 is located at a numerical value of 80. The pointer 20 is to be located between the symbols 32 and 34 when the electrologist is again operating in the face technic range. The path 30 between the symbols 32 and 34 is colored a specific color, such as orange, which is consistent with the meter face 14. Similarly, the path 30 between the symbol 36 and the numerical value 90 is colored green, with the pointer 20 to be located in this position when the electrologist is operating on portions of the human body other than the face. The numerical value of 40 is to indicate the average minimum starting point when operating on the face. The electrologist can then adjsut either upward or downward from that position. The reason for adjustment is in direct relation to the pain threshold of the particular patient. The more sensitive a patient is, the lower value that will normally be used. The more the patient is able to withstand pain, the higher the value that will be used.

The probe 42 is to be inserted within the hair follicle 44 directly adjacent the hair shaft 46. The tip of the probe 42 is to be located directly adjacent the bulb 48 of the hair shaft 46. The bulb 48 includes a papilla 50.

Mounted within the face of the housing 12 are cataphoresis plugs 52 and 54. An electrical grounding connector is to be located within the plug 54, with a positive electrical member connected to plug 52. Inscribed directly adjacent the plug 52 is a symbol 56 which is to represent the cataphoresis technique which will be explained further on in the specification. A symbol 58 is located adjacent the plug 54, which is to represent the ground for the cataphoresis.

To assist the electrologist to generally orient as to which portion of the housing 12 represents the electrical positive connections, and as to which side represents the electrical negative connections, there is located a positive representation symbol 60 on the left side of the housing 12, with an electrically negative representative symbol 62 located on the right side of the housing 12.

Located directly adjacent the symbol 60, there is a plug 64, which also has a symbol 66 located thereby. On the right hand side of the housing 12, there is located a socket 68 which has symbol 70 located directly adjacent thereto. The needle 42 is connected to an electrical cord (not shown) which is in turn plugged into the socket 68. The symbol 70 is a graphic representation of the needle and its attached cord, while the symbol 66 is a graphic representation of the ground cord, which is to be held by the patient.

Located beneath the meter face 14 is an indicator light 80, which is to be lit when direct current electrolysis circuitry of the machine 10 is being utilized. The electrolysis circuitry is to be turned on and off by an on-off switch 74. Mounted directly adjacent the indicator light 80, is a control knob 82, which is to be adjusted by the electrologist so as to change the position of the pointer 18 with respect to the path 22.

Similarly, when on-off switch 74 is moved to the on position, indicator light 72 is also activated. Mounted directly adjacent indicator light 72 is a control knob 76, which the electrologist can adjust to move the needle 20 across the path 30.

Referring particularly to FIG. 3 of the drawings, there is shown a block diagram of the electrical circuitry of the present invention. Generally, the electrical circuitry is to be connected to a source of electricity (not shown) through the use of a conventional electrical plug 84. The electrical plug 84 supplies electrical energy to the direct current electrolysis circuit 86 and also to the radio frequency thermolysis circuit 88. Both circuits 86 and 88 feed directly to needle 42.

Figure 4:
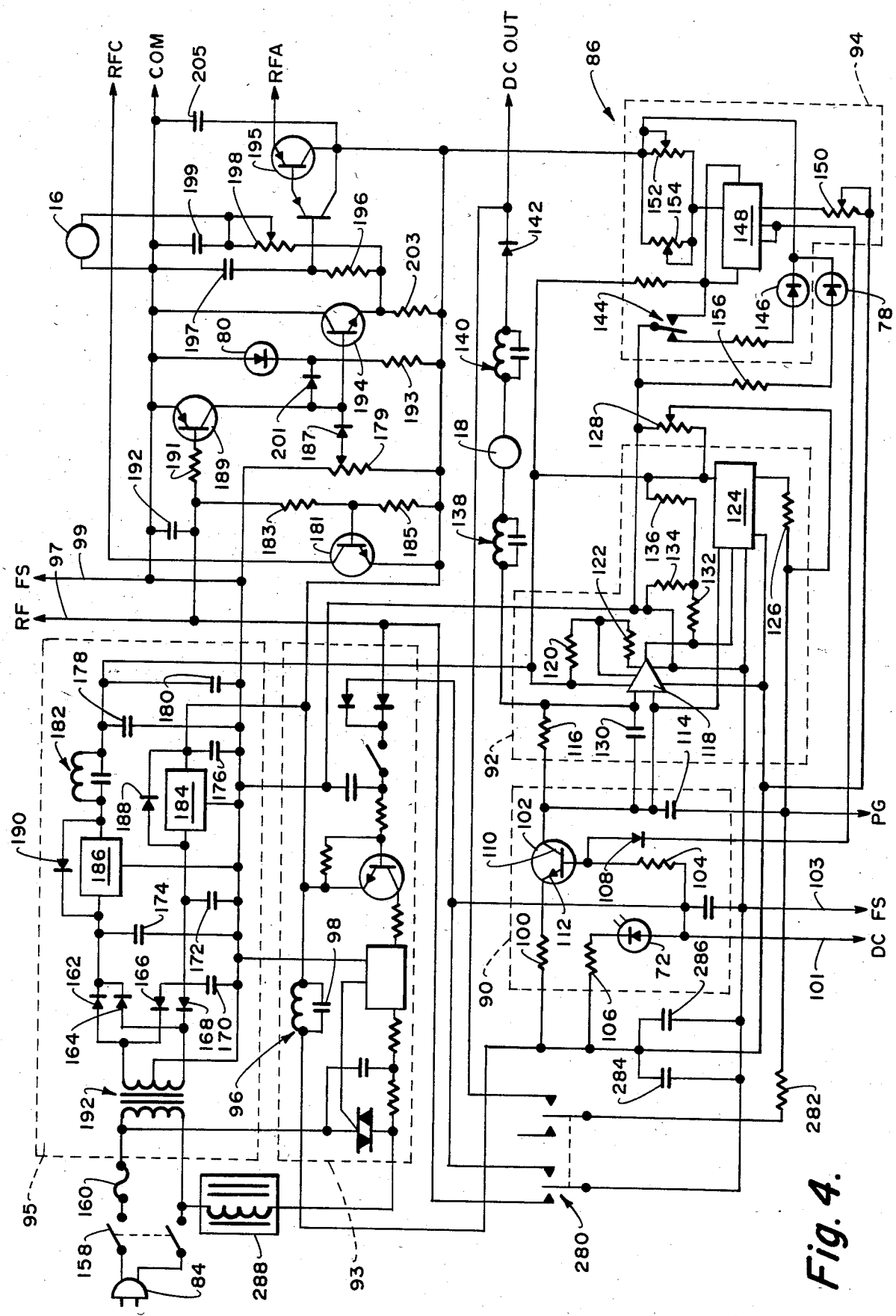
FIG. 4 is the electrical circuit diagram for the direct current circuit of the electrolysis machine of this invention.

Referring particularly FIG. 4 of the drawings, there is shown the DC circuit 86. In designing this circuit 86, there are certain factors that had to be taken into consideration. One factor was that a maximum current was wanted of no more than two milliamps to prevent shocking of the patient. Also, the output current should be independent of a load resistance. The electrical resistance of the patient is not constant as electrical resistance changes as the patient becomes uncomfortable, nervous, tired, and so forth. Therefore, the DC circuit 86 includes a current control represented by dotted area 90. Also when the current is activated to avoid shocking the patient, the current should rise slowly (from one half second to one second in time). This slow rise is obtained through the use of circuitry which is represented generally within dotted line area 92. The circuitry confined within dotted line area 94 is directed to adjusting of blending of the DC circuit with the radio frequency circuit. The circuitry of dotted area 93 comprises the air pump control circuitry, while dotted area 95 denotes the power supply.

A conventional footswitch (not shown) is to be used by the electrologist and is to operate the radio frequency through conductors 97 and 99. Another footswitch operates the DC circuit through conductors 101 and 103. A constant bias of −18 volts is supplied through a first filter composed of a twelve microhenrys (uh) inductor 96 and a 12 picofarad (pf) capacitor 98. This first filter is also part of the air pump control circuitry 93. The −18 volts bias is then supplied through a kilo-ohm (K) resistor 100. The resistor 100 connects with the emitter 112 of a transistor 102. A separate voltage path connects between the resistor 100 to a 10K resistor 104. This separate path also connects through a 1K resistor 106 and a diode 108. The diode 108 functions to counterbalance the emitter base junction of the transistor 102, as well as also to compensate for thermal drift. When the circuit heats up, the voltage drop across the junction of the transistor tends to shift. This could also cause a shift in current on the collector side of the transistor. The diode compensates for this shift.

The voltage across resistor 106 equals the voltage across resistor 100. By utilizing this voltage divider, the current can be controlled at the collector 110 of the transistor 102. If the voltage at variable resistor 150 is set at zero by completely bypassing resistor 100, then the voltage across resistor 100 will be the same and will get no current from transistor 102. Similarly, any preset position value established by the resistor 106 will supply an appropriate current to the collector 110 of the transistor 102. It is to be noted that the current in the collector 110 is approximately equal to the current of the emitter 112.

With the supply voltage of approximately −18 volts, the human body resistance can vary up to eight to ten thousand ohms without interfering with operation of the transistor 102. If the resistance increases much beyond that, the transistor 102 will go into saturation and no longer function accurately.

As previously mentioned, it is necessary to have the current rise slowly to its desired level in order to avoid shocking the patient. This can be obtained through the use of capacitor 114 which is has been selected to be at a value of 47 microfarad (mf). The output of the current from the collector 110 functions to charge the capacitor 114. As the capacitor 114 gradually charges, the current shunts to the patient. Therefore, a slow DC current rise has been obtained.

However, there is an additional problem in that sometimes the patient will inadvertently release the patient ground which is the return electrical path to the DC current circuit 86. When this happens, the transistor 102, trying to overcome the increased electrical resistance, saturates and drives itself to within a volt of the −18 volts and in so doing charges the capacitor 114 to also this value. When the patient recontacts the ground, the capacitor 114, having no where else to go, discharges into the patient and causes a surge of current in excess of two and a half milliamps. This amount of current is too high to be considered safe. Some treatments in sensitive areas, such as the face or around the eyes, the electrologist must use no more than one half a milliamp. Therefore, in those areas, any surge at even a milliamp is considered to be potentially dangerous.

To avoid this kind of surge from occuring, a separate electrical path was inserted in connection with the capacitor 114. If the current could be diverted in another direction, then the transistor 102 could be kept out of saturation and it would continue to operate and keep the capacitor 114 from charging up.

Placed within the output path to the patient is a 1K resistor 116. This resistor 116 serves as a current sensing resistor, as the voltage across this resistor is proportional to the current to the patient. This voltage is generated across the comparator 118 which is a device that, at negative volts, puts out an output of zero and when the voltage goes positive, it immediately becomes a +5 volts. By use of trimming resistors 120 and 122 which are respectively 3K and 5.6K, the comparator 118 can be set so that it goes to zero, the voltage when it is negative is low and it becomes zero, or positive, it goes to a +5 volts. This +5 volts triggers the analog switch 124. The triggering of the switch 124 completes the diversion circuit path by causing the electrical current to flow through 5.6K resistor 126 and through variable resistor 128 to ground. Normally when the current slows to the patient, there is a negative voltage created across resistor 116. As a result the analog switch 124 remains open. When the current stops, the comparator goes to its +5 volts which closes analog switch 124 and the alternate path is created.

By adjusting of the resistor 128 to lower than normal patient resistance, it has been avoided that the capacitor would charge up to any value higher than what would be seen at the patient for that particular current setting. Resistor 128 is needed for restart capacity. If the electrical energy went straight to ground without resistor 128, there would be no reason for the current to go to the patient. A certain potential needs to be developed to allow a current path when the patient recontacts the electrical ground.

When the patient recontacts the ground, there is a parallel network for a short period of time. A certain amount of the electrical current goes through resistor 128 and a certain amount shunts off to the patient through resistor 116. When the voltage is sensed across resistor 116, once again a negative voltage is obtained which results in the comparator 118 dropping back to zero, which then opens the analog switch 124. By the setting of the resistor 128 a slight bit lower than the patient body resistance, a slow current rise on reactivation of the circuit is obtained. This slow current rise is not as slow as when the circuit is intially activated, but it is slow enough to prevent shocking the patient.

The capacitor 130, having a value of 0.01 mf, serves to stablize this diversion circuit when subjected to radio frequency interference. Since a radio frequency circuit is incorporated in conjunction with the electrolysis machine of this invention, it is to be understood that this diversion circuit will be constantly subjected to radio frequency interference.

The 1K resistor 132 and 1K resistor 134 function as pull-up resistor, which means that they help the comparator pull-up or reach the level of +5 volts. Also included is a biasing resistor 136. This diversion circuit proved to be fairly sensitive to radio frequency and when the radio frequency was activated, this circuit was normally disabled. Therefore, it was necessary to filter the direct current output to the patient to protect the patient from the radio frequency. The radio frequency is about 13 megahertz (mh). Frequencies at this level radiate and do not follow a wire. It was found that simple shunt capacitors, which normally provide entire radio frequency protection, could not be relyed on in conjunction with this diversion circuit.

It was found that to avoid this radio frequency interference, it was necessary to have a radio frequency block on every wire coming into the direct current circuit. There is one such filter represented by inductor 96 and capacitor 98 having already been described. However, there are two other similar filters 138 and 140 located between the resistor 116 and the probe 42. Between the filters 138 and 140 there is located the pointer 18 of the meter. the diode 142 is located between the filter 140 and the probe 42 to positively assure that there will be no electrical current from the radio frequency which will connect between the diode 142 and the probe 42.

When the operator activates switch 144 on the control panel of the housing 12, the additional circuitry 94 is activated, which is to automatically blend the radio frequency and the direct current circuitry together. This automatic blending position is depicted by switch 144 within FIG. 4 of the drawings. If the switch 144 is not in this position, the direct current and the radio frequency are supplied independently and can be adjusted independently.

With the switch 144 in the position shown in FIG. 4, the light emitting diode 146 is activated. The light emitting diode 146 is also mounted on the control panel of the housing 12. Analog switch 148 (which is the same unit as switch 124, except using different connections) is then caused to increase in potential from 0 to 15 volts. The switch 148 then disconnects potentiometer 150 and then connects variable resistor 152. Trimming potentiometer 154 is wired in parallel with the potentiometer 152 for calibration purposes. The potentiometer 154 gives the operating technician the capability of setting the value of the radio frequency to the direct current and this value of the radio frequency is automatically supplied to the patient according to the particular setting for the direct current.

It is to be noted that there is a light emitting diode which functions as an indicator light 78 on the face of the control panel. Indicator light 78 is utilized in conjunction with resistor 156 to indicate that power is being supplied to the entire unit.

Electrical current from the plug 84 is to be supplied through a double throw switch 158 an through a fuse 160 to power supply circuitry 95. The power supply circuitry is deemed to be conventional and need not be described in any specific detail. The supply circuitry 95 is composed of a series of unidirectional diodes 162, 164, 166 and 168, filtering capacitors 170, 172, 174, 176, 178 and 180, a filter 182 and voltage regulators 184 and 186. The unidirectional diode 188 is associated with regulator 184 and unidirectional diode 190 is associated with voltage regulator 186. The power supply circuitry also includes transformer 192.

The output from the power supply circuitry 95 is to be supplied, upon depressing the radio frequency footswitch to transistor 181. The activation of the transistor 181 is to supply 18 volts to the radio frequency circuitry shown in FIG. 5. Associated with the transistor 181 are biasing resistors 183 and 185. Variable resistor 179, which is controlled by control knob 82 mounted on the control panel, is to permit the operator to manually adjust the setting of the radio frequency. The diode 187 prevents feedback of the radio frequency.

When the radio frequency foot-switch is activated, an electrical short is created across light emitting diode 80. The transistor 189 is then activated. A biasing resistor 191 is associated with the transistor 189, as well as a filtering capacitor 192. A current limiting resistor 193 is also included in the circuit with the light emitting diode 80.

Activation of transistor 189 removes the electrical ground from the diode 187. This causes variable resistor 185 to supply voltage between 1.4 volts and 18 volts to the base of transistor 194. From the emitter of the resistor 194, the voltage varies from 0 to 16 volts. This causes the transistor 195 to adjust from 0 to 15 volts. Resistor 196 and capacitor 197 causes the voltage at the base of transistor 195 to rise slowly (between one half and three seconds). This is so that not only does the direct current to the patient rise slowly, but also the radio frequency.

The variable resistor 198 is used to calibrate the meter 16. The capacitor 199 functions to dampen the movement of the pointer of the meter 16.

A unidirectional diode 201 connects the transistor 189 between light emitting diode 80 and resistor 193. Biasing resistor 203 is associated with the transistor 194. Filter capacitor 205 is associated with transistor 195. It is to be understood that the output terminals RFC, COM and RFA connect into similar terminals of FIG. 5.

It is desirable that the electrologist can make an initial setting of both values for the radio frequency and the direct current prior to initiating supplying of such to the patient. The electrologist can made a determination depending upon the size of the individual, previous experience, as well as sex of the patient and make a reasonable determination as to the amount of radio frequency and the amount of direct current that the patient can stand. In order to accomplish this, the electrologist activates test switch assembly 280. Once the desired anticipated levels of both the radio frequency and direct current have been established by the electrologist's turning of control knobs 76 and 82, the electrologist releases the test switch 280 and then proceeds to supply both the direct current and the radio frequency to the patient. The resistor 282 is utilized in conjunction with the test switch 280 to simulate the resistance of the patient during activation of the test circuit. Also associated with the test circuit are filtering capacitors 284 and 286.

After the electrologist has performed the desired amount of removal of hair, the electrologist is to soothe the applied area through the application of a jet of air. This jet of air is to be supplied through an air pump 288, through an appropriate hose (not shown) to the particular desired area on the patient. The air pump 288 is operated through an air pump circuitry 93 which need not be explained in detail since it is deemed to be conventional. Actually, the use of the air pump 288 is not deemed to constitute any specific part of this invention. The air pump 288 is turned on by switch 63 mounted on the control panel.

The locating of 0.01 pf capacitors at different locations throughout this direct current circuitry is for reasons to eliminate interference by the radio frequency.

Referring particularly to FIG. 5 of the drawings, there is shown a radio frequency thermolysis circuit 88. Transistor 200 within this circuit is a crystal oscillator. This crystal oscillator 200 is biased by a 47K resistor 202. The transistor 200 is driven by a 13,560 killohertz fundamental mode crystal 204. The oscillator tank circuit composed of 2.2 mh inductor 206 and 3.9 pf capacitor 208 is trimmed by capacitor 210. The capacitor 210 is adjustable from 3.5 to 20 pf.

The tolerance of the crystal 204 is plus or minus 0.678 killohertz. Capacitor 212 functions to trim the resistance of the crystal 204 to typically 13,562 killohertz.

The 47 pf capacitor 214 couples with the output of oscillator 200 to untuned buffer 216. The buffer 216 provides a constant load to oscillator 200. Buffer 216 is biased by 100K resistor 218, 220 ohm resistor 220 and 100 ohm resistor 222. The buffer 216 is loaded by 12 mh inductor 224 and a 100 pf coupling capacitor 226. The buffer 228 is a common emitter amplifier biased by 6.3K resistor 230 and 330 ohm resistor 232. Buffer 228 drives a tank circuit consisting of 8 pf capacitor 234 and toroidal transformer 236. Toroidal transformer 236 is trimmed by capacitor 238. Capacitor 238 is adjustable to between 3.5 and 20 pf. The transformer 236 provides a low output impedance to drive the base of amplifier 240, which is mounted in parallel with 56 ohm resistor 242. The amplifier 240 drives a printed circuit strip line inductor 244 and a tank circuit which includes 680 pf capacitor 246. The high capacitance of this tank circuit reduces the effect of the primarily capacitive load of the probe inserted into the patient's hair follicle so that the final radio frequency amplifiers tank circuit is not substantially detuned.

The actual construction of the probe 42 consists of a seventy-two inch length of co-axial cable whose end shield is unconnected and whose end center conductor is connected to a fine wire for insertion into a hair follicle according to normal electrological practice.

The 0.01 mf capacitor 248, 150 mh inductor 250 and 0.01 mf capacitor 252 function as a radio frequency filter. Also, 0.01 mf capacitor 254, 150 mh inductor 256 and 0.01 mf capacitor 258 function as a filter for radio frequency.

What is claimed is:

1. An electrolysis machine comprising:

a probe adapted to be located directly adjacent the hair follicle; and electrical circuitry electrically connected to said probe, said electrical circuitry comprising a first circuit and a second circuit, said first circuit producing a direct current output, said second circuit producing a radio frequency output, said second circuit being completely independent of said first circuit, said first circuit including first circuit means for slowing the rise of direct current to the patient upon initial establishment of a direct current circuit with the patient, said second circuit including second circuit means for slowing the rise of radio frequency to the patient upon initial establishment of a radio frequency circuit with the patient; and current control means included within said first circuit for controlling the current of said direct current output, said current control means including a by-pass electrical circuit path, said by-pass electrical circuit path including means for preventing current build-up within said first circuit which occurs upon loss of the electrical ground of said probe, said by-pass electrical circuit path also including means for activating said means for preventing upon sensing of a substantially increased electrical resistance of the patient, upon reconnection with the electrical ground by the patient the patient is not electrically shocked.

2. An electrolysis machine as defined in claim 1 wherein:

manually operated switch means connecting said first circuit and said second circuit, said manually operated switch means being movable between a first position and a second position, with said manually operated switch means in said first position said second circuit being controllable separate from said first circuit, with said manually operated switch means in said second position said second circuit being automatically controlled in conjunction with controlling of said first circuit.

* * * * *